United States Patent [19]

Cook et al.

[11] Patent Number: 4,817,868
[45] Date of Patent: Apr. 4, 1989

[54] CARRIER FOR SCENTED MATERIAL

[75] Inventors: John M. Cook, Lafayette, Calif.; Lon L. Weiss, Kinnelon, N.J.

[73] Assignee: Dow Corning Corp., Midland, Mich.

[21] Appl. No.: 58,907

[22] Filed: Jun. 5, 1987

[51] Int. Cl.$^4$ .............................................. A61L 9/04
[52] U.S. Cl. ...................................... 239/55; 239/57
[58] Field of Search .................... 239/34, 36, 53–57, 239/60

[56] References Cited

U.S. PATENT DOCUMENTS

| 2,234,062 | 3/1941 | Roberts | 239/36 |
|---|---|---|---|
| 2,629,628 | 2/1953 | Vaillancourt | 239/53 |
| 3,098,703 | 7/1963 | Snyder et al. | 239/60 |
| 3,272,533 | 9/1966 | Allen | 239/56 |
| 3,441,353 | 4/1969 | Claff | 239/36 |
| 3,643,371 | 2/1972 | Gordon | 43/131 |
| 3,661,326 | 5/1972 | Wilson | 239/60 |
| 3,823,873 | 7/1974 | Miller, Jr. et al. | 239/54 |
| 3,940,062 | 2/1976 | Rainey | 239/56 |
| 3,949,515 | 4/1976 | Mitchell et al. | 43/121 |
| 3,987,577 | 10/1976 | Hardee | 43/121 |
| 4,017,030 | 4/1977 | Coplan et al. | |
| 4,144,309 | 3/1979 | Langston et al. | 239/54 |
| 4,283,878 | 8/1981 | Hill et al. | |
| 4,523,870 | 6/1985 | Spector | 239/57 |
| 4,611,425 | 9/1986 | Dickerson | 43/121 |
| 4,715,536 | 12/1987 | Capizzi et al. | 239/54 |

FOREIGN PATENT DOCUMENTS

| 529536 | 8/1956 | Canada | 239/36 |
|---|---|---|---|
| 0011924 | 11/1980 | European Pat. Off. | |
| 0122054 | 10/1984 | European Pat. Off. | |
| 0152190 | 8/1985 | European Pat. Off. | |
| 1585307 | 1/1970 | France | |
| 2213733 | 9/1974 | France | |
| 316618 | 7/1929 | United Kingdom | 239/55 |
| 2042340 | 9/1980 | United Kingdom | |
| 2056272 | 3/1981 | United Kingdom | |

Primary Examiner—Andres Kashnikow
Assistant Examiner—Michael J. Forman
Attorney, Agent, or Firm—Steele, Gould & Fried

[57] ABSTRACT

A dispenser for broadcasting a scent is particularly useful in connection with insect pheromones, a quantity of volatile pheromone carrying substance is packaged as a solid or gel in a hollow tube. A carrier can be provided for the tube, having a surface to which the tube is to be affixed with the longitudinal axis of the tube substantially parallel to the surface of the carrier, and the tube being disposed directly on the surface of the carrier. The carrier has at least one air circulation opening aligned perpendicular to the longitudinal axis of the tube and one or more stops preventing relative displacement of the tube and the carrier. Preferably, the carrier is a one piece integrally molded thermoplastic panel, with retaining clasps projecting from a planar body and adapted to bear diametrically inwardly on the tube. The length of the tube and dimensions of the carrier are such that the tube positively remains captive. Users are provided with substantially marginal area on the planar body adjacent the tube for manual manipulation, as needed, for example, to install the scent dispenser in a trap.

12 Claims, 2 Drawing Sheets

CARRIER FOR SCENTED MATERIAL

BACKGROUND OF THE INVENTION

1. Field of the Invention

This invention relates to the field of carriers for controlled release of scents, and in particular to a cylindrical or preferably tube-like scent body mounted in a tab-like carrier for deploying concentrated attractive insect pheromones, for example to be disposed in an insect trap.

2. Prior Art

Insect traps are known in which various compositions are used to attract the insects to the trap. The compositions may involve bait substances in which insects are drawn to a trap seeking food, or pheromones, to which the insects are drawn for purposes of reproduction. It is possible in connection with trapping boll weevils to combine pheromone attraction with food attraction by concentrating the boll weevils at preliminary plots of cotton. The insects are attracted to food at the trap plot, and the boll weevil aggregating pheromone encourages the insects into a trap.

Boll weevil traps are the subject of U.S. Pat. Nos. 3,949,515-Mitchell; 3,987,577-Hardee and 4,611,425-Dickerson. Traps of this type for use in the disclosed procedures have become standard equipment. Similarly, pheromone traps for gypsy moths are widely available as a common product.

Attractive artificially produced pheromones are known for various insects. These include, for example, the male attractive pheromone Grandlure for boll weevils, Dispar Lure for gypsy moths, Trimedlure for medflies, Gossyplure for pink boll worms and others. Pheromones are also available for oriental fruit moths and diamond back moths. Many other insects are subject to attractive pheromones, natural or artificial. The proclivities of the insects are used together with their instinctive response to pheromones for urging the insects into appropriate traps. For example, boll weevil traps are painted yellow, which is in itself attractive, and the insect's tendency to move geotropically upwardly into a collector is used to concentrate the insects in an enclosure at the top of the trap. A funnel shaped entrance is used so insects in the enclosure cannot readily find the exit. Tendencies of various insects are thus known and used, wherein insects are at least part concentrated using pheromones. The requirements in each case with pheromones are to locate the scent source in a trap and to broadcast the attractive pheromone scent to a wide area in which the insects are otherwise located.

Pheromones according to known techniques have been packed in laminated sheet-like sections with volatile scent-releasing material comprised in one or more laminate layers, and in cylindrical bodies or plugs in which the whole bodies are composed of scent releasing material. The tendency with any scent releasing substance is quite logically to employ a large surface area configuration in order to maximize the surface area exposed to air diffusing through the area. However, exposed scent-releasing surface area can present problems in the handling of pheromones. Some pheromones are effective attractive agents even at very low concentrations. Also, pheromones and their carriers can be toxic, particularly if taken orally or brought into contact with mucous membranes. These characteristics of insect pheromones make is undesirable to produce a pheromone lure in which the scented material is exposed on all available exterior surfaces, which could maximize dispersal. Persons handling the pheromones, particularly due to their high concentration at the source and low threshold effective concentration, must be careful to avoid contact, which also could result in various unintended lure locations, for example on outer surfaces of a trap.

A solid composition apt for entrapping scented chemicals such as insect pheromones is disclosed in commonly-owned patent applications Ser. No. 915,749 filed Oct. 6, 1986 and Ser. No. 053,609 filed May 20, 1987. This composition is useful for entrapping various chemicals in a solid body, providing for their sustained release. A functional group is entrapped in the lattice of a cross-linked hydrophobic polymer during the polymerization of the monomers forming the polymer lattice. This composition can entrap insect pheromones in the polymer, which results in a sustained pheromone-releasing solid. According to the present invention, such a composition can be packaged conveniently by in situ polymerization in a plastic tube. The pheromone is emitted at the ends, while the tube can be handled safely provided care is taken to avoid contact with the composition inside the tube. By controlling the dimension of the tube such as the length, diameter and relative proportion of the lumen of the tube occuppied by the pheromone-emitting solid composition, the rate of release of insect pheromone (or other scent) can be controlled. The tube can be supplied in a length from which single trap doses are cut, or the tube can be supplied in individual doses, for example with closed ends that are opened to commence broadcasting the pheromone. Enveloping a pheromone composition in a tube departs from the prior art tendency to maximize surface area, but has proved quite effective.

The packaging or mounting of insect attractive pheromones and other scented materials in a tube physically supports the pheromone or the like, and allows a user to have at least some protection from direct contact with the pheromone, namely by engaging the tube-and-pheromone packaged lure only by its sides remote from its two opposite ends. Handling of the tubes is not foolproof because the preferred tubes for holding the insect attractive pheromones and the like are normally quite small (e.g. 0.5-2.0 cm length and 0.3 cm diameter). Therefore, it can still be difficult to avoid contact with the pheromone material in the lure when handling the tubes. Use of pheromone lures requires certain manual steps, including installation of individual lures in insect traps and the like. One user may have a large number of traps to service. According to the present invention, a pheromone-carrying material such as a tube lure holding a pheromone-releasing composition is mounted on an additional carrier structure having a substantial marginal area for manipulation by the user. The carrier portion of the dispenser has certain structural features that retain the lure safely in position and allow appropriate air circulation adjacent the tube ends. The structural features likewise allow the user to conveniently install the carrier directly in certain known insect traps such as the standard Dickerson boll weevil trap. The attractive material is easily handled and safe from loss from exposed to the air for release of scent.

By facilitating the use of entrapped pheromone compositions, and by allowing technique for accurate sustained release without waste, the invention provides an efficient and practical means for handling and dealing with insect attractive pheromones.

SUMMARY OF THE INVENTION

It is an object of the invention to provide an inexpensive and effective carrier for scent-releasing compositions.

It is another object of the invention to allow use of effectively very high concentrated scent-emitting substances, while allowing for accurate release of predetermined concentrations.

It is also an object of the invention to facilitate manual handling of means carrying high concentration scented material and to avoid propagating the scent into unwanted areas.

It is another object of the invention to prevent loss or waste of pheromone lure materials.

It is still another object of the invention to reduce the expense of using attractive insect pheromones in insect traps, and ultimately to reduce the use of broad based insecticides in favor of means directed to control specific insect pests.

These and other objects are accomplished by a dispenser for broadcasting a scent, particularly useful in connection with insect pheromones, wherein a quantity of volatile pheromone carrying substance is packaged in a hollow tube, for example by in situ polymerization in the tube of a solution of monomers for entrapping the pheromone with volatile scent carriers. The tube can be air impervious or porous, or a porous tube holding pheromone composition can be disposed in a nonporous one. The device preferably further includes a carrier for the tube, having a surface to which the tube is to be affixed with the longitudinal axis of the tube substantially parallel to the surface of the carrier, the tube being disposed directly on the surface of the carrier. The carrier has at least one air circulation opening aligned perpendicular to the longitudinal axis of the tube and one or more stops obstructing excess movement of the tube along its axis and preventing relative displacement of the tube and the carrier. Preferably, the carrier is a one piece integrally molded thermoplastic panel, with retaining clasps projecting from a planar body and adapted to bear diametrically inwardly on the tube. The length of the tube and dimensions of the carrier are such that the tube positively remains captive. Users are provided with substantial marginal area on the planar body adjacent the tube for manual manipulation, as needed, for example, to install the scent dispenser in a trap.

BRIEF DESCRIPTION OF THE DRAWINGS

There are shown in the drawings the embodiments which are presently preferred. It should be understood that the invention is not limited to the precise arrangements and instrumentalities shown in the drawings and that the invention within the scope of the claims is subject to arrangements in a variety of alternative groupings of features. In the drawings.

DETAILED DESCRIPTION OF THE PREFERRED EMBODIMENTS

Figure 1:
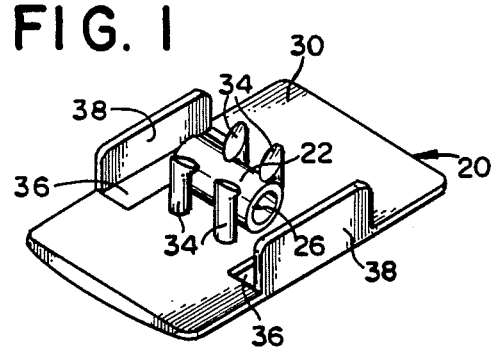
FIG. 1 is a perspective view of a preferred dispenser according to the invention, with a scented material carried in a tube attached to a carrier as shown.

A dispenser 20 for broadcasting a scent, is shown in FIG. 1 to include a means 22, preferably a hollow tube, holding a scented material such as a polymer-entrapped pheromone. The pheromone is in turn supported on a holder 30, to which the tube 22 is attached. Means other than a hollow tube are also possible for holding a scented material on a carrier tab, for example the scented material being supplied in a solid cylindrical form. Similarly, a tube enclosure can be employed on other forms of carriers. It is preferred in accordance with the invention that the scented material be a polymerized solid or gelled material partly enclosed by a tube, thereby avoiding direct contact between the scented material and handling equipment and persons manipulating the dispenser. It is also possible to closely control the rate of scent emission by altering the geometry of the tube including its length, diameter, porosity and relationship to the holder 30. The tube preferably encloses the scented material except at two opposite ends of the tube, and can be supplied in a length or in cut pieces.

Dispenser 20 accepts lure materials to emit any of various scents. The dispenser is especially apt for emission of attractive insect pheromones. The dispenser 20 is loaded with an appropriate quantity of scented material, for example a solid volatile sustained release material in the form of an in situ polymerized solid or a strip or cylinder placed in tube 22 disposed on carrier 30 and in turn placed inside an insect trap (not shown). Insects drawn to the attractive pheromone are captured in the trap and can be poisoned, sterilized or otherwise processed.

As shown in FIG. 1, the lure tube 22 is affixed to the planar body 32 of carrier or holder 30 by means of resilient pins 34. Pins 34 are located and spaced such that they bear inwardly on tube 22, and position tube 22 with one or both of the open ends 26 of tube 22 exposed to appropriate air circulation allowing the emission of scent. Preferably, air circulation holes 36 through planar body 32 are disposed adjacent the open ends 26 of tube 22. These allow air to pass through the carrier panel and over ends 26 of tube 22 and/or simply space the ends of the tube at a slight distance from the nearest surface. Raised stops 38 are located at a space from either end of tube 22 along the longitudinal axis of tube 22, preventing escape of the tube from dispenser 20, by longitudinal displacement of the tube sufficient to clear resilient pins 34.

Figure 3:
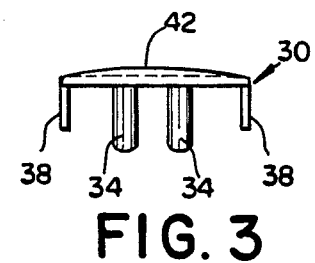
FIG. 3 is an end view of the device of FIG. 1, shown inverted and illustrating a preferred contour of the back surface.
Figures 2, 4:
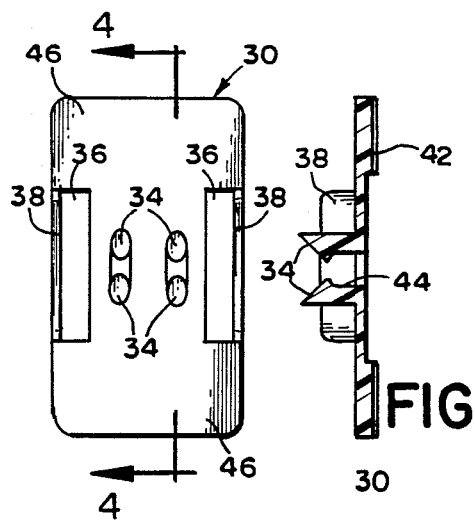
FIG. 2 is a plan view of the carrier of FIG. 1.
FIG. 4 is a section view taken along lines 4—4 in FIG. 2.

The carrier or holder 30 apart from dispensing tube 22 is shown in FIGS. 2-4. FIG. 2, a plan view, shows the arrangement of pins 34, air circulation holes 36 and stops 38. The distance between either set of pins 34 and the nearest stop 38 is preferably less than the length of a lure tube to be placed therein. Therefore, the tube cannot become free of pins 34. Stops 38 and pins 34 also project above the level of the tube and thereby tend to prevent accidental contact with a tube or other form of scent containing material mounted between pins 34. Large marginal areas 46 are available for the user to grasp the holder 30 well clear of the scent carrying material area.

FIGS. 3 and 4 show the relative heights of the pins 34 and stops 38 in end view and section view, respectively. FIG. 3 also shows a preferred arrangement for a rear side of the carrier 30, wherein radius areas 42 are provided, such that the carrier 30 fits in surface contact with the curved internal wall of a typical insect trap. Typical traps for boll weevils, mentioned hereinabove, are characterized by cup-like or generally-spherical enclosures in which the attractive insect pheromone is to be placed and towards which the insects move.

According to the preferred embodiment of the invention, a mounted hollow tube polymer entrapped dispenser for scented material is provided in place of the usual planar laminate of scent-containing material or typical wick to be wetted with liquid scented compositions normally placed in a trap enclosure. The radius wall 42 of carrier 30 can be provided with a contact adhesive to attach carrier 30 with its attached lure 22 on an inner surface of the trap enclosure. It is also possible to arrange the back wall of the carrier 30 to be curved in two perpendicular planes, for use in a spherical enclosure insect trap. The embodiment shown in FIGS. 2-4, however, is only curved in one plane, being appropriate for a cylindrical enclosure insect trap.

Carrier 30 and its pins 34 are shown in section view in FIG. 4. The pins 34 are molded integrally with the carrier body, being provided with projections adjacent distal ends of pins 34 such that a slightly larger space 44 is defined between pins 34 immediately adjacent the surface of the carrier than adjacent the distal ends. In this way, the tube (not shown in FIG. 4) can be simply pressed between pins 34, where it will remain captive so long as pins 34 are not pressed away from one another. Preferably, carrier 30 is an integral molding of a thermoplastic polymer. Openings immediately between facing sets of pins 34 are provided for ease in molding, mold pins being located in this area during molding such that the proper contour for the facing portions of pin 34 can be defined in the mold. The carrier material can be any suitable thermoplastic polymer such as a high or low density polyolefin, for example polyethylene, polypropylene, etc., a polyester, phenolic resin, a copolymer such as styrene-butadiene, etc. The polymer composition is chosen for ease of molding and in order to provide a flexible carrier so that the pins can bear inwardly but can be separated when the lure material is pressed between them. The preferred material is high density polyethylene.

It is presently preferred that the carrier be provided in various different colors, allowig the user to keep track of dates on which the carriers are installed. For example, a user who employs a number of insect traps can install only new scent-releasing dispensers of a single color at one time, and a different color next time, therefore avoiding any confusion as to the age and possible depletion of the scented material.

The scented material itself can be a lattice-entrapped composition for example as disclosed in U.S. pat. appln. Ser. No. 915,749 filed Oct. 6, 1986. This material can be provided in the form of a cylindrical length placed within a hollow tube 22 by in situ polymerization or by installation in tube 22 after hardening. The scent material can be smaller than the internal diameter or lumen of the tube, allowing air passage over the surface of the scented material, or the scented material can be smaller than the lumen of the tube or arranged to shrink. The scented material can be carried in a porous inner tube to be placed in an impervious outer tube 22. Should the scented material be dimensioned or carried in an inner tube such that it is normally displaceable in tube 22, the fact that stops 38 are located along the longitudinal axis at either end of the tube will present loss of the scented material. The stops likewise prevent loss of the tube in the same way.

Preferably, either an inner tube or an outer tube 22 form a polymerization mold for the pheromone-carrying material. Preferably, the material of tube 22 cannot be permeated by the polymerization bath solution, normally containing water, glycerine and oil. An appropriate material for an impervious tubing is polytetrafluoroethylene (Teflon). Should the tubing be permeable to the polymerization solution, the permeable tubing can be placed in a larger diameter tubing that is not permeable. Furthermore, the permeable tubing can be placed in the impermeable tubing prior to addition of the polymerization medium. According to this technique, the impervious tubing can be used to transfer heat from the polymerization medium to the contents of the permeable tubing thus causing polymerization of the pheromone-entrapped monomers. According to presently preferred embodiments, polytetrafluoroethylene is advantageously employed for tubing 22. Other possible impervious tubing materials are polyethylene, polypropylene and chlorinated polyvinyl chloride. Permeable tubing may be made from polyvinyl chloride, polyethylene or polypropylene, especially provided the tubing is made thin. Other possibilities are styrene, ethylene vinyl acetate and copolymers including the foregoing materials.

Preferably, the tubing is filled with a lattice-entrapped pheromone composition either using a syringe or by a vacuum system. According to the vacuum system, one end of a long length of tubing is simply inserted into a container containing the monomers and active pheromone scented ingredients, and a vacuum is applied to the opposite end. In this way, the composition is drawn into the tubing along its entire length. The ends are then sealed to allow polymerization in the tube, for example by melting the ends using a bunsen burner to soften the polymer, whereupon pliers can be used to clamp the ends of the mold to close the tubing, sealing the mixture inside.

Use of tubing as a sustained release means gives a longer and steadier release rate than exposed bodies of active material or laminated layers. The polymerized tubing core material can, however, be used as a controlled release agent by itself. Preferably, the material is polymerized in situ and remains in place, the ends of the tubing being cut to expose the active ingredients. Assuming impermeable tubing, only two circular end sections are exposed, thus greatly reducing the surface area through which volatile materials can be released. Accordingly, the overall lure lasts longer as the volatile materials from the space between the ends of the tube reaches the ends. The rate of release is also relatively constant. A permeable or semi-permeable tubing can also be employed, increasing the rate of release. If the tubing is permeable by the active ingredient in the pheromone composition (i.e., if the active ingredient includes a solvent for the tubing polymer, the surface area includes the ends plus at least a percentage of the surface area of the tube, as exposed). The rate of release of the active ingredient from the ends will be higher per unit area than through the tubing, and concentrations released from these two surfaces will be cumulative. In any event, the invention provides a very easy way to manufacture lures containing small amounts of active scented ingredients such as pheromones and the like. This tubing can be employed apart from carrier 30 or, preferably, on carrier 30, both the tube and the carrier being convenient means for manipulating pheromone-containing bodies and providing protection for persons using the lure.

Figure 6:
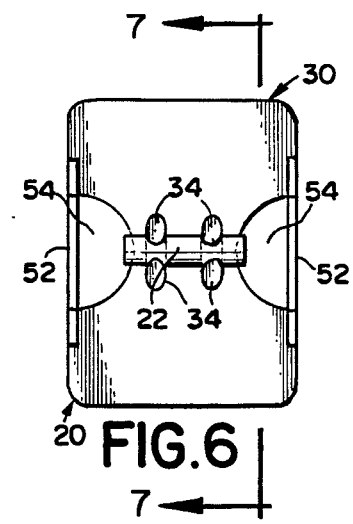
FIG. 6 is a plan view of the device of FIG. 5.
Figure 5:
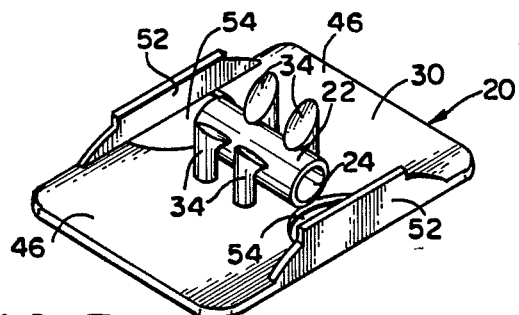
FIG. 5 is a perspective view of an alternative carrier and tube according to the invention.
Figure 7:
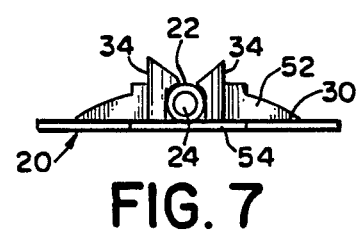
FIG. 7 is a section view taken along lines 7—7 in FIG. 6.

An alternative embodiment of the invention in which a tube 22 is mounted on an alternative carrier is shown in FIGS. 5–7. Dispenser 20 as before includes a scented material preferably in the form of a hollow tube 22 with pheromone or the like 24 located therein. The tube is captive between pins 34 on carrier 30, which defines enlarged marginal portions 46 for handling by the user. In this embodiment, circular air circulation holes 54 are disposed at either open end of tube 22. Tube 22 can protrude outwardly from the body of the carrier into the open area over air circulation holes 54 as shown in FIG. 6. Preferably, the scent carrying means such as tube 22 and the pheromone or other contents 24 (as shown in FIG. 7) are dimensioned such that tube 22 and/or contents 24 are longer than the space between pins 34 and closest side wall 52 of carrier 30. Accordingly, the scented material cannot be lost from the tube and the tube cannot be lost from the carrier.

FIG. 7 shows a section view along the area of an air circulation hole 54. Unlike the embodiment of FIGS. 1–3, wherein the rounded rear surface at ends 42 tended to hold the planar body of carrier 30 somewhat above a surface to which the carrier is affixed, FIG. 7 shows an embodiment with a flat rear surface. It may be advisable in connection with a flat surface to avoid gluing the carrier directly to a rear facing surface, thereby defeating the possibility of air circulation through holes 54. It is possible, however, to affix the carrier in plane such that some space is allowed underneath carrier 30, improving scent emission.

In each of the embodiments of FIGS. 1–3 and 5–7, the scent emitting lure is a relatively small volume of the overall dispenser package. In each case, the scented material retaining pins 34 and the stops 38, 52, respectively, are dimensioned to extend somewhat beyond the scented material, minimizing the possibility of accidental contact with the scented material. Therefore, very high concentration attractive pheromones can be employed, and their rate of emission can be closely controlled by the dimensions of the respective elements.

Figure 8:
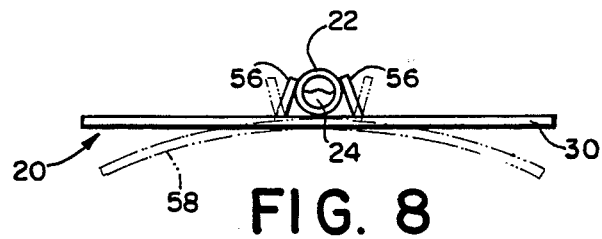
FIG. 8 is a side view of a carrier, showing the flexing of the clasp pins together with the carrier body, the flexed condition of the body and pins being shown in broken lines.

The carrier 30 of dispenser 20 as shown in FIG. 8 is flexible. FIG. 8 shows an alternative possibility, wherein the pins 56 are cylindrical rather than provided with projecting sections adjacent the distal ends. In any event, facing pairs of pins 56 define a larger area in the space between them adjacent the carrier body 30, and a smaller area adjacent the distal ends, thereby holding scented material 24, preferably disposed in tube 22, immediately next to the carrier. Alternatively, a cavity can be defined by an enlargement between the pins at a space from the carrier. In each of these embodiments, the carriers are flexible and the tube 22 or other material can be removed by flexing carrier 30 as shown in FIG. 8. Flexed carrier 58 is characterized by outwardly flaring pins, allowing the escape of trapped tube and/or body of scented material. Carriers 30 are quite inexpensive and not practically subject to re-use. However, should the user so desire, the scented material can be removed from the carrier in this manner and replaced.

Figure 9:
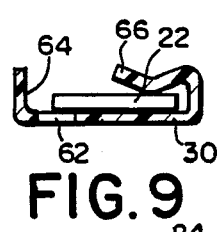
FIG. 9 is a section view of an alternative embodiment in which the clasp means are a resilient extension of the planar carrier body.
Figure 10:
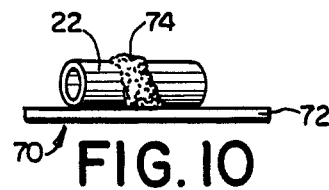
FIG. 10 is an elevation view of a further embodiment of the invention, wherein the tube is glued to the carrier.
Figure 11:
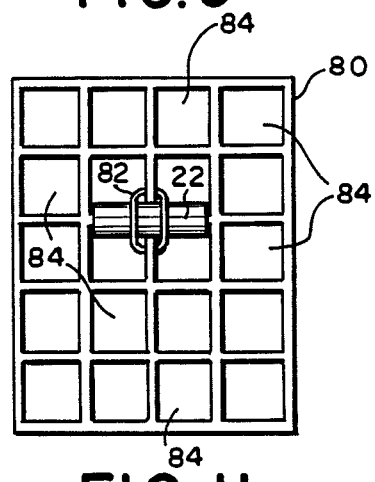
FIG. 11 is a plan view of a further alternative embodiment, the tube being affixed to a carrier grid by means of a linear element.

FIGS. 9–11 show some additional alternative embodiments using other means for carrying pheromone tubes. In FIG. 9, a scented material carrier 22 is disposed in a carrier 30 such that only one of the opposite ends is directly exposed to an air circulation hole 62. A resilient extension 66 of carrier 30 bears downwardly on scented material 22, holding it captive. A stop 64 limits the extent to which scented material body 22 can be relatively displaced on carrier 30. As in the other embodiments, stop 64 is located on the far side of an air circulation opening 62, whereby the end of scented material 22 is located over the air circulation hole.

In FIG. 10, dispenser 70 includes a simple panel 72 without air holes, but having a scented material bearing tube 22 disposed on a surface. Tube 22 in FIG. 10 is simply glued to panel 72, with the axis of the tube parallel to the plane body 72.

Another alternative embodiment is shown in plan view in FIG. 11. Tube 22 in this case is affixed to a grid 80, the grid 80 defining a plurality of holes 84, each of which functions to allow air circulation through and around the dispenser. Tube 22 can be adhesively affixed as in FIG. 10 or affixed as shown using an elastomeric band or the like wrapped around the grid-defining lengths of the carrier 80. Tube 22 can also be used apart from any carrier.

The dispenser of the invention is subject to additional alternatives, and combinations of features in different groupings. In each case, the dispenser is much easier to handle than the very small, liquid or otherwise inconvenient scented material dispensers known. The user's fingers do not touch the active ingredients in the lure, thereby avoiding safety problems and possible loss of the lure by displacement of the lure material or its tube in the carrier. Should displacement occur accidentally, the device is nevertheless arranged to prevent complete loss. In the event displacement is to be positively prevented, it is possible to graft the pheromone trapping polymer to the tube. The clips hold even loosely-enclosed sustained release scented material in place between the side stops, which prevent loss of the material or tube even in the event the carrier is slightly flexed. Displacement from the tube may affect the rate of release.

It is most convenient to supply concentrated scent-emitting materials in the form of a tube or the like enclosing high concentration sustained release agents. The carrier and captive element according to the invention are most versatile with respect to possible placement in typical traps. For example, the device as shown in FIG. 1 can be placed in the collection cup on the top of a boll weevil trap, or on the inner wall of the bottom cup in the trap. The back side of the lure can be curved to match the radius of standard insect traps, allowing for dependable attachment of the carrier to the trap, for example in the bottom cup. This also allows multiple lures to be placed in a cup, whereby the trap remains useful and the user can monitor the seasonal history of each trap. Placing lures for example in a boll weevil trap on the inside of the bottom cup rather than in the collection cup on the top of the typical boll weevil trap is easier, faster and is just as effective as placement in the top cup. The side vents allow for maximum air circulation, improving volatilization of the active attractive scent. Even when the lure is attached flat to the bottom cup of a boll weevil trap, the air circulation vents space the ends of the tube above the surface of the trap, improving circulation. The device is effective and convenient.

The invention having been disclosed herein, skilled persons will arrive at various improvements and modifications for particular application. Reference should be made to the appended claims rather than the foregoing specification for indicating the true scope of the invention.

What is claimed is:

1. A device for controlled release of pheromone scent, comprising:
    a pheromone material emitting a volatile insect-attractive pheromone scent, the material being disposed in a tube, the tube having at least end openings at which the material is exposed to air circulation;
    a carrier for the material, the carrier being a plate shaped as a substantially planar sheet and having a side to which the tube is affixed, the carrier having a substantial margin adjacent the tube, the carrier having a through hole disposed perpendicularly through said plate at least at one of the end openings of the tube, and means holding the tube on said side, whereby the carrier can be manipulated with reduced exposure to the material and the pheromone scent is broadcast by air circulation at said through hole.

2. The device of claim 1, wherein the carrier is an integrally molded plastic tab, the carrier having a through hole disposed through the tab at both of the end openings of the tube, the through holes being defined by an opening bounded along an outer periphery of the carrier by a raised stop, the stop restricting relative displacement of the tube and the carrier.

3. The device of claim 1, wherein the means holding the tube on said side include a clasp means on the carrier, the clasp means having opposed posts extending from the carrier and bearing inwardly toward one another and against the tube, the clasp means affixing the scented material to the carrier.

4. A dispenser for broadcasting a insect-attractive pheromone scent, comprising:
    a hollow plastic tube partly enclosing a volatile material carrying the pheromone scent, the tube having a longitudinal axis and two opposite ends, the volatile material being a scent-entrapping non-flowing material disposed along the axis between the ends; and,
    a carrier for the tube, the carrier being a substantially planar plate having a side to which the tube is affixed, the longitudinal axis of the tube being substantially parallel to the plate when the tube is affixed, the carrier having at least one opening aligned perpendicular to the longitudinal axis of the tube and arranged adjacent at least one of said two opposite ends.

5. The dispenser of claim 4, wherein the scent-entrapping non-flowing material is an in situ polymerized composition having a functional scented pheromone entrapped in a lattice.

6. The dispenser of claim 4, further comprising a pair of posts extending substantially perpendicular from the carrier, the posts bearing inwardly toward one another to resiliently engage the tube.

7. The dispenser of claim 6, wherein the posts define an opening for the tube by means of depressions on each of said posts facing one another, the tube being engaged in the depressions.

8. The dispenser of claim 6, wherein the carrier is a continuous panel.

9. The dispenser of claim 6, wherein the carrier is a grid of resilient material.

10. The dispenser of claim 4, further comprising an insect trap, the dispenser being installed in the insect trap.

11. An insect lure dispenser, comprising:
    an attractive material lure including an attractive insect pheromone disposed in a hollow tube open at opposite ends for exposure to ambient air, the pheromone being an entrapped lattice polymer with a volatile scent-carrying agent entrapped in a polymeric lattice within the tube; and,
    a carrier for holding the attractive lure material, the carrier being a planar tab having a body and means for holding the tube adjacent the body, the carrier having at least one air circulation opening disposed adjacent the tube at one end of the tube, and means for affixing the lure to the body in the form of a pair of opposed posts bearing inwardly toward one another and downwardly on the tube toward the tab.

12. A device for controlled release of pest control scented material, comprising:
    a pest control scented material emitting a volatile attractive pest control scent, the material being disposed in a tube, the tube having two opposite end openings at which the material is exposed to air circulation;
    a carrier for the material, the carrier being a substantially planar plate having a side to which the tube is laid flat and affixed, the carrier having a substantial margin adjacent the tube, the carrier having a through hole through the plate, disposed at least at one of the end openings of the tube and means holding the tube on said side, whereby the carrier can be manipulated with reduced exposure to the material and the scent is broadcast by air circulation at said through hole.

* * * * *